US010254300B2

(12) United States Patent
Birrer et al.

(10) Patent No.: US 10,254,300 B2
(45) Date of Patent: Apr. 9, 2019

(54) ANALYZER AND METHOD FOR LOADING A RACK INTO A RACK SLOT OF AN ANALYZER

(71) Applicant: Roche Molecular Systems, Inc., Pleasanton, CA (US)

(72) Inventors: Armin Birrer, Udligenswil (CH); Rolf Frey, Ebikon (CH); Christian Marty, Goldau (CH); André Peter, Meggen (CH); Marco Sangermano, Kriens (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/498,020

(22) Filed: Apr. 26, 2017

(65) Prior Publication Data

US 2017/0315145 A1 Nov. 2, 2017

(30) Foreign Application Priority Data

Apr. 27, 2016 (EP) ..................................... 16167270

(51) Int. Cl.
*G01N 35/02* (2006.01)
*G01N 35/00* (2006.01)
(Continued)

(52) U.S. Cl.
CPC ..... *G01N 35/026* (2013.01); *G01N 35/00623* (2013.01); *G01N 35/04* (2013.01);
(Continued)

(58) Field of Classification Search
CPC ...... G01N 35/026; G01N 35/02; G01N 35/00; G01N 35/00623; G01N 35/00613; G01N 35/00594; G01N 35/00584
(Continued)

(56) References Cited

U.S. PATENT DOCUMENTS 5,209,903 A * 5/1993 Kanamori ............ G01N 1/2813
422/44
5,232,081 A * 8/1993 Kanamori .............. G01N 35/04
198/347.1
(Continued)

FOREIGN PATENT DOCUMENTS

DE 202012010656 1/2013
EP 0738541 B1 1/2002
(Continued)

OTHER PUBLICATIONS http://www.diasorin.com/en/immunodiagnostic-solutions/systems/clia-systems/liaisonr-xl, obtained on May 24, 2016.
(Continued)

*Primary Examiner* — Christine T Mui
(74) *Attorney, Agent, or Firm* — Eric Grant Lee; Pamela Ancona

(57) ABSTRACT

An analyzer is disclosed. The analyzer comprises a rack slot configured to receive at least one rack, wherein the rack slot comprises a front end, at which the rack is manually loadable into the rack slot, and a rear end, which is opposite to the front end and at which the rack is fully receivable in the rack slot, and a spring device arranged at the rear end, wherein the spring device is configured to provide a biasing force towards the front end, wherein the biasing force is adapted to move the rack towards the front end if not fully received in the rack slot, wherein the spring device is configured to fix the rack in a final position if the rack is fully received in the rack slot. Further, a method for loading a rack into a rack slot of an analyzer and a system comprising an analyzer and a computer controller are disclosed.

14 Claims, 4 Drawing Sheets

(51) Int. Cl.
*G01N 35/04* (2006.01)
*G01V 8/10* (2006.01)

(52) U.S. Cl.
CPC ..... *G01V 8/10* (2013.01); *G01N 2035/00752* (2013.01); *G01N 2035/00801* (2013.01); *G01N 2035/0412* (2013.01); *G01N 2035/0465* (2013.01)

(58) Field of Classification Search
USPC ............... 422/65, 63, 50; 436/48, 47, 43
See application file for complete search history.

(56) References Cited

U.S. PATENT DOCUMENTS

| | | | |
|---|---|---|---|
| 5,720,377 | A | 2/1998 | Lapeus et al. |
| 7,628,954 | B2 | 12/2009 | Gomm et al. |
| 8,551,404 | B2 | 10/2013 | Nagai et al. |
| 8,685,322 | B2 | 4/2014 | Griebel et al. |
| 2006/0216198 | A1 | 9/2006 | Koike |
| 2006/0216199 | A1 | 9/2006 | Koike |
| 2006/0245865 | A1 | 11/2006 | Babson |
| 2012/0118954 | A1 | 5/2012 | Hagen et al. |
| 2014/0174208 | A1 | 6/2014 | Coleman et al. |
| 2014/0209677 | A1 | 7/2014 | Clark et al. |

FOREIGN PATENT DOCUMENTS

| | | |
|---|---|---|
| EP | 1883822 | 4/2009 |
| EP | 2752247 A2 | 7/2014 |
| JP | 3181083 U | 1/2013 |
| JP | 05698466 B2 | 4/2015 |
| WO | WO2010132045 A1 | 11/2010 |

OTHER PUBLICATIONS

MagNA Pure 96 System Operators Manual (LSR) 3.0 SW 3.0 and Addendum: MagNA Pure 96 User Training Guide, Version 3.0, MagNA Pure 96 Operator's Guide, Version 3.0, Jun. 2014/ Addendum Nov. 1, 2015, p. 1-213.
Search Report for EP16167270.4 dated Nov. 10, 2016.

* cited by examiner

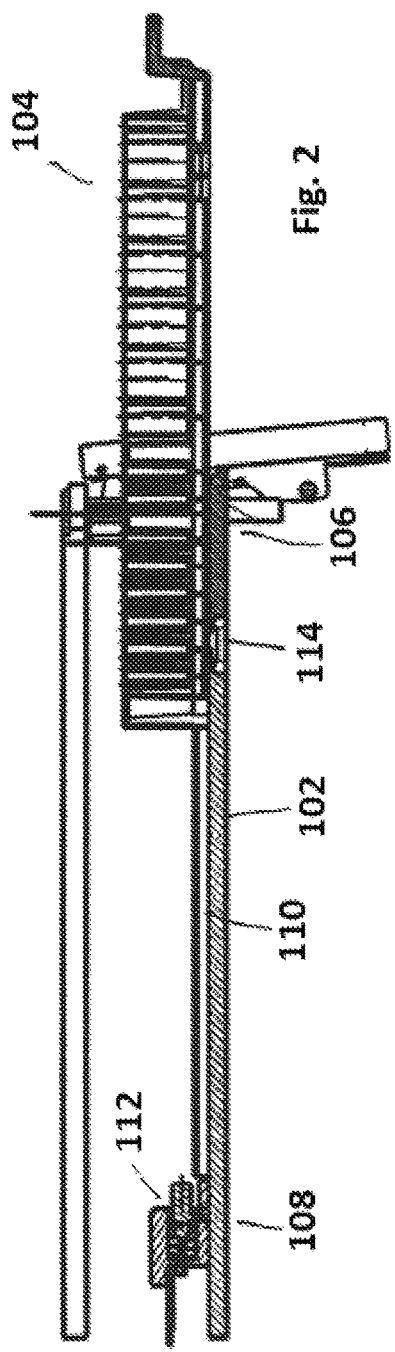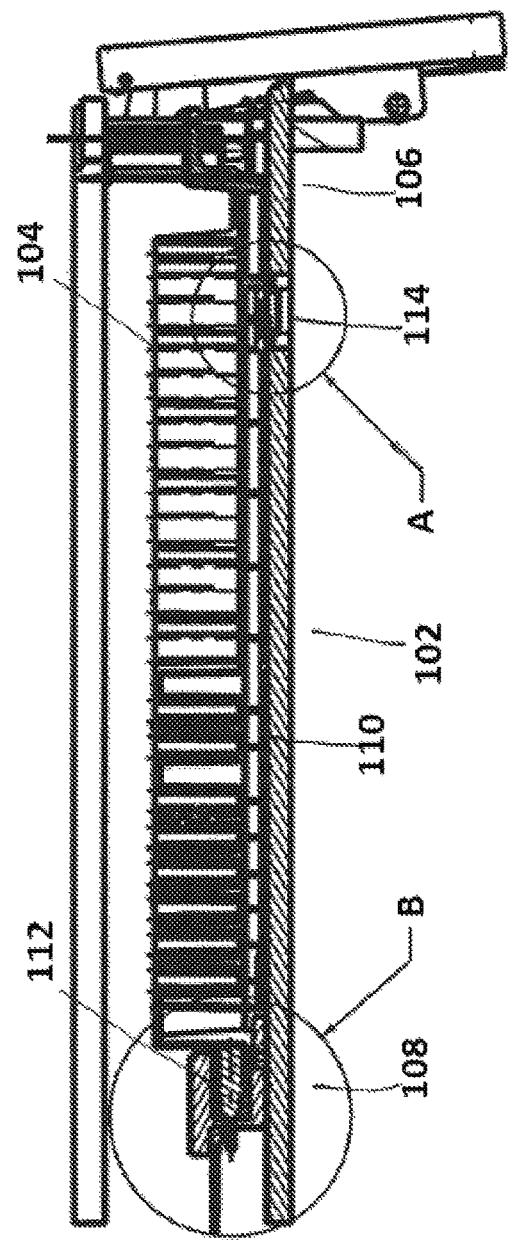

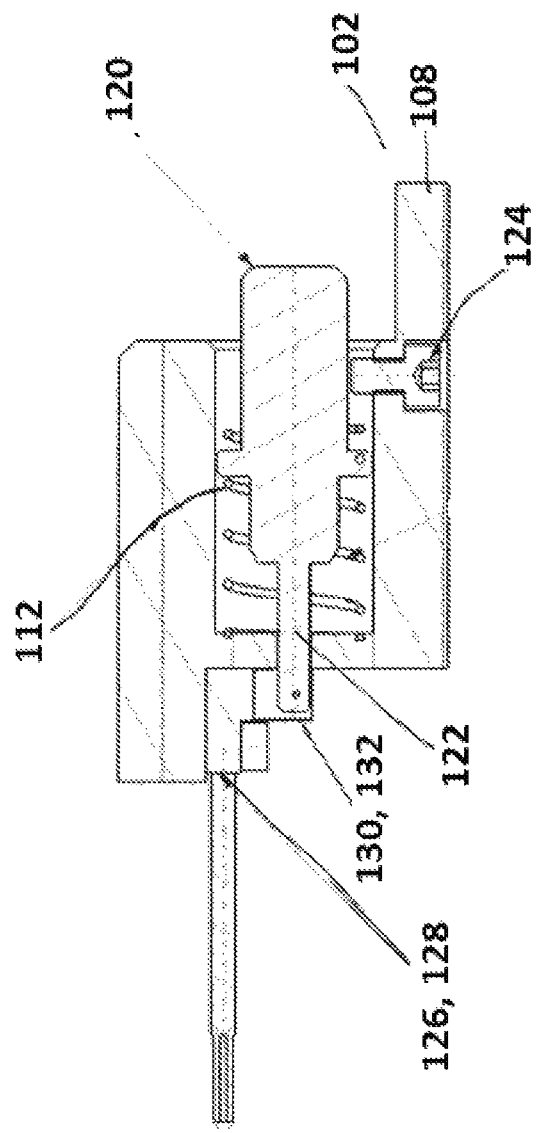

ANALYZER AND METHOD FOR LOADING A RACK INTO A RACK SLOT OF AN ANALYZER

CROSS-REFERENCE TO RELATED APPLICATION

The present application claims the benefit of priority under 35 U.S.C. § 119(a) of EP 16167270.4, filed Apr. 27, 2016, the entire disclosure of which is hereby incorporated by reference.

FIELD OF THE DISCLOSURE

The present disclosure relates to an analyzer and a method for loading a rack into a rack slot of an analyzer.

RELATED ART

Modern analyzers are based on automated sample processing systems that permit high throughput specimen processing. Such systems not only permit greatly increased sample processing throughput but also decrease the number of samples that cannot be analyzed, decrease the manual labor and allow for productive use of an operator's "walk away time" during sample processing. Such analyzers usually comprise a rack slot into which a rack may be inserted, wherein the rack comprises a plurality of sample vessels such as sample tubes.

EP 0 738 541 B1 describes an analyzer comprising a plurality of rack slots into which racks holding a plurality of sample vessels may be inserted. When racks are loaded into an analyzer, a barcode reader is often used for identifying the rack ID, position ID and sample ID. A lock or sensor is required to trigger the bar code reader or to keep the rack in its final position. Using such automated analyzers provides advantages concerning the handling. Nevertheless, there are still some drawbacks. Such analyzers are cost intensive and they miss robustness against frequent manual loading processes. Thus, user convenience is not sufficient.

SUMMARY OF THE DISCLOSURE

The present disclosure provides an analyzer comprising a rack slot configured to receive at least one rack, wherein the rack slot comprises a front end, at which the rack is manually loadable into the rack slot, and a rear end, which is opposite to the front end and at which the rack is fully receivable in the rack slot, and a spring device arranged at the rear end, wherein the spring device is configured to provide a biasing force towards the front end, wherein the biasing force is adapted to move the rack towards the front end if not fully received in the rack slot, wherein the spring device is configured to fix the rack in a final position if the rack is fully received in the rack slot.

The following specific embodiments of the analyzer are contemplated:

The rack slot can be configured such that the rack is moveable between the front end and the rear end in a longitudinal direction. The rack slot can also include an elastic snap fit device configured to engage the rack if the rack is in the final position. The spring device can be configured to fix the rack in the final position by pushing the rack against the snap fit device. The snap fit device engages a depression on a lower side of the rack. The rack slot can include a sliding surface on which the rack is slidably moveable between the front end and the rear end, wherein the snap fit device is located at the sliding surface. The snap fit device can be moveable between a protruded position, in which the snap fit device protrudes from the sliding surface for engaging the lower side of the rack if the rack is in the final position, and a retracted position, in which the snap fit device does not protrude from the sliding surface if the rack is loaded into the rack slot and not in the final position. The snap fit device can be adjacent the front end.

The analyzer can also include a bar code reader for reading a rack identification, a position identification, an identification of a sample, reagent or consumable provided in the rack, and/or a compartment identification of the rack. The analyzer further comprises a sensor configured to detect whether the rack is in the final position. In a specific embodiment, the sensor is configured to trigger a reading process of the bar code reader; the sensor is arranged adjacent the rear end; the sensor is configured to detect whether the rack is in the final position by means of detecting a compressed state of the spring device; and/or the sensor is a light barrier.

The spring device can include a plunger and a plunger rod moveable together with the spring device, wherein the light barrier is configured to detect the compressed state of the spring device by means of detecting the plunger rod. The light barrier can include a light emitter and a light receiver, wherein the light emitter is configured to emit light on a light path towards the light receiver, wherein the light barrier is configured to detect the plunger rod if the light receiver is not capable of receiving light from the light emitter. The light barrier can also be configured to trigger the reading process of the bar code reader if the light barrier detects that the rack is in the final position. The plunger rod can be moveable such that the light path is interruptible.

Also contemplated is a method for loading a rack into a rack slot of an analyzer as described herein, comprising (a) manually loading a rack at the front end of the rack slot, (b) manually moving the rack to the rear end of the rack slot against the biasing force of the spring device, and (c) fixing the rack in the final position by means of the spring device when the rack is fully received in the rack slot. In the method contemplated herein, the rack can be engaged by an elastic snap fit device when the rack is in the final position. The spring device can fix the rack in the final position by pushing the rack against the snap fit device. The snap fit device can engage a depression on a lower side of the rack. Moreover, the snap fit device protrudes from a sliding surface of the rack slot for engaging the lower side of the rack when the rack is in the final position within the rack slot, wherein the snap fit device does not protrude from the sliding surface when the rack is loaded into the rack slot and not in the final position.

The method can also include the step of reading a rack identification, a position identification, an identification of a sample, reagent or consumable provided in the rack, and/or a compartment identification of the rack by means of a bar code reader. The method further comprises detecting whether the rack is in the final position by means of a sensor. For example, the sensor triggers a reading process of the bar code reader. In addition or alternatively, the sensor detects whether the rack is in the final position by means of detecting a compressed state of the spring device. Moreover, the spring device comprises a plunger and a plunger rod moveable together with the spring device, and the method includes detecting, via the light barrier, the compressed state of the spring device by detecting the plunger rod. The sensor can be a light barrier and comprises a light emitter and a light receiver, wherein the light emitter emits light on a light path towards the light receiver, wherein the light barrier detects the plunger rod if the light receiver does not receive light from the light emitter. In the method described herein, the plunger rod can be moved such that the light path is interrupted when the rack is in the final position. In addition, the sensor triggers the reading process of the bar code reader if the sensor detects that the rack is in the final position.

Also provided is a system including an analyzer as described herein and a computer controller configured to supervise a loading process of a rack into the rack slot of the analyzer. The computer controller is configured to detect whether the rack is in the final position. The system can further include a signalizing device configured to signalize a correct and/or incorrect loading of the rack, wherein the analyzer comprises a sensor configured to detect whether the rack is in the final position, wherein the sensor is connected to the computer controller. Moreover, the analyzer can include a bar code reader for reading a rack identification, a position identification, an identification of a sample, a reagent or a consumable provided in the rack, and/or a compartment identification of the rack by means of a bar code reader, wherein the bar code reader is connected to the computer controller. Still further, the sensor can be configured to trigger the bar code reader if the rack is in the final position. Moreover, the system can further comprise a signalizing device configured to signalize a correct and/or incorrect loading of the rack.

The disclosure further provides an analyzer including a rack slot configured to receive a rack, wherein the rack slot comprises a front end adapted to receive the rack, a rear end opposite the front end, and a spring device positioned at the rear end, wherein the spring device provides a biasing force towards the front end to move the rack towards the front end and thereby position and fix the rack in the rack slot if the rack is fully received in the rack slot.

Also provided is a method for loading a rack into a rack slot of an analyzer as described herein, comprising (a) loading, manually, a rack at the front end of the rack slot, (b) moving, manually, the rack to the rear end of the rack slot against the biasing force of the spring device, and (c) fixing the rack in position by means of the spring device when the rack is fully received in the rack slot.

Moreover, the disclosure contemplates a system comprising an analyzer as described herein operably connected to a computer controller configured to control a loading process of a rack into the rack slot of the analyzer.

BRIEF DESCRIPTION OF THE FIGURES

Further features and embodiments of the disclosure are disclosed in more detail in the subsequent description of embodiments, preferably in conjunction with the dependent claims. Therein, the respective features are realized in an isolated fashion as well as in any arbitrary feasible combination as the skilled person may realize. The embodiments are schematically depicted in the figures. Therein, identical reference numbers refer to identical elements or functionally identical elements.

FIG. 2 shows a side view of a rack slot of the analyzer.
FIG. 3 shows a further side view of the rack slot.
FIG. 6 shows a further enlarged view of detail B of FIG. 3.

DETAILED DESCRIPTION OF THE EMBODIMENTS

Figure 1:
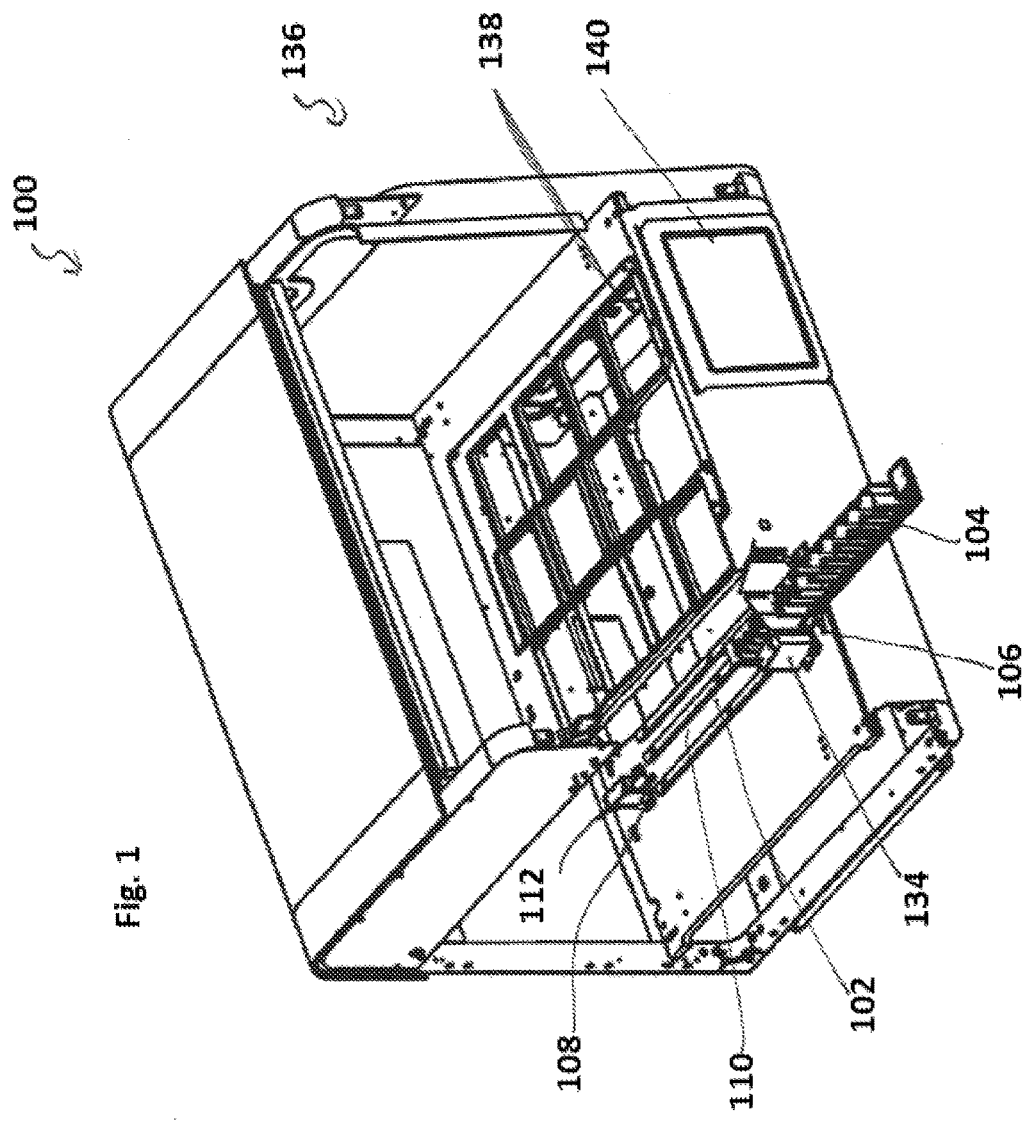
FIG. 1 shows a perspective view of an analyzer.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B," and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one," "one or more," or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

According to the present disclosure, an analyzer comprises a rack slot configured to receive at least one rack, wherein the rack slot comprises a front end, at which the rack is manually loadable into the rack slot, and a rear end, which is opposite to the front end and at which the rack is fully receivable in the rack slot, and a spring device arranged at the rear end, wherein the spring device is configured to provide a biasing force towards the front end, wherein the biasing force is adapted to move the rack towards the front end if not fully received in the rack slot, wherein the spring device is configured to fix the rack in a final position if the rack is fully received in the rack slot.

As the spring device fixes the rack in the final position, a robust positioning of the rack is provided. Further, unless the rack is in the final position, the spring device is configured to push the rack rearwards, i.e. towards the front end. Thus, the spring device gives a kind of mechanical feedback whether the rack is completely or correctly inserted in the rack slot or not. Thereby, a premature and incorrect starting of an analyzing process of samples provided in the rack is prevented.

The rack slot may be configured such that the rack is moveable between the front end and the rear end in a longitudinal direction. Thus, in order to move the rack into the final position, the rack merely has to be linearly moved against the biasing force of the spring device. Thereby, the risk of incorrectly inserting the rack is minimized.

The rack slot may comprise an elastic snap fit device configured to engage the rack if the rack is in the final position. Thus, the fixation of the rack in the final position is facilitated.

The spring device may be configured to fix the rack in the final position by means of pushing the rack against the snap fit device. By pushing the rack against the snap fit device, the spring device ensures an exact positioning of the rack at the final position. Particularly, the rack may not deviate from its position during an analyzing process such that any interruptions of the analyzing process due to a positional shift are avoided.

The snap fit device may be configured to engage a depression on a lower side of the rack. Thus, by means of a simple positive fit, the positioning of the rack at the final position is ensured.

The rack slot may comprise a sliding surface on which the rack is slidably moveable between the front end and the rear end, wherein the snap fit device may be located at the sliding surface. Thus, the snap fit device may engage the rack along a path being as short as technically possible.

The snap fit device may be moveable between a protruded position, in which the snap fit device protrudes from the sliding surface for engaging the lower side of the rack if the rack is in the final position, and a retracted position, in which the snap fit device does not protrude from the sliding surface, if the rack is loaded into the rack slot and not in the final position. Thus, engaging the lower side by the snap fit device is provided by protruding from the sliding surface and disengaging is provided by not protruding from the sliding surface. Particularly, unless the rack is in the final position, the lower side of the rack presses the snap fit device downwards in the retracted position such that the snap fit device does not obstruct the inserting or loading of the rack into the rack slot.

The snap fit device may be arranged adjacent the front end. As the distance between the front end and the rear end corresponds to at least a length of the rack, the rack may be pushed by the spring device against the snap fit device with almost the complete length thereof.

The analyzer may further comprise a bar code reader for reading a rack identification, a position identification, an identification of a sample, reagent or consumable provided in the rack and/or a compartment identification of the rack. Thus, the analyzer is configured to obtain different information directly or indirectly associated with the rack by means of the bar code reader as bar codes are commonly used with racks, samples stored therein and the like.

The analyzer may further comprise a sensor configured to detect whether the rack is in the final position. Such a construction enables the initiation of any analyzing process only in case the rack is completely and correctly inserted into the rack slot.

The sensor may be operably connected to the bar code reader and therefore, configured to trigger a reading process of the bar code reader if the rack is correctly positioned in the rack slot. Thus, the bar code reader is only activated if the sensor indicates that the rack is completely and correctly inserted into the rack slot. Thereby, any potential reading errors are prevented. Further, energy may be saved if the bar code reader is not permanently activated.

The sensor may be arranged adjacent the rear end. Thus, the sensor is close to the final position which facilitates the detection process.

The sensor may be configured to detect whether the rack is in the final position by detecting a compressed state of the spring device. Thus, the spring device indicates the final position of the rack if the spring device is compressed.

The sensor may be a light barrier. Thus, it is possible to detect whether the rack is in the final position or not by means of a well established technical device, which facilitates the installation of the sensor.

The spring device may comprise a plunger and a plunger rod moveable together with the spring device. The light barrier may be configured to detect the compressed state of the spring device by means of detecting the plunger rod. Thus, depending on whether the plunger rod is detected or not, the sensor can detect whether the rack is in the final position or not.

The light barrier may comprise a light emitter and a light receiver. The light emitter may be configured to emit light on a light path towards the light receiver. The light barrier may be configured to detect the plunger rod if the light receiver is not capable of receiving light from the light emitter. Thus, if the light receiver does not receive light, the sensor indicates that the rack is in the final position. Accordingly, the correct and complete insertion the rack into the rack slot may be detected.

The plunger rod may be moveable such that the light path is interruptible. Thus, an interruption of the light path indicates the final position of the rack and if the plunger rod exposes the light path, this indicates that the rack is not fully received in the rack slot.

The light barrier may be configured to trigger the reading process of the bar code reader if the light barrier detects that the rack is in the final position. Thus, the bar code reader is only activated if the sensor indicates that the rack is completely and correctly inserted into the rack slot. Thereby, any potential reading errors are prevented. Further, energy may be saved if the bar code reader is not permanently activated. Accordingly, a user friendly loading of a rack into the rack slot of the analyzer is provided.

According to the present disclosure, a method for loading a rack into a rack slot of an analyzer comprises (a) manually loading a rack at the front end of the rack slot, (b) manually moving the rack to the rear end of the rack slot against the biasing force of the spring device, and (c) fixing the rack in the final position by means of the spring device when the rack is fully received in the rack slot.

Thus, a robust and user friendly loading concept is provided.

The rack may be engaged by an elastic snap fit device when the rack is in the final position. Thus, the fixation of the rack in the final position is facilitated.

The spring device may fix the rack in the final position by pushing the rack against the snap fit device. By pushing the rack against the snap fit device, the spring device ensures an exact positioning of the rack at the final position. Particularly, the rack may not deviate from its position during an analyzing process such that any interruptions of the analyzing process due to a positional shift are avoided.

The snap fit device may engage a depression on a lower side of the rack. Thus, by means of a simple positive fit, the positioning of the rack at the final position is ensured.

The snap fit device may protrude from a sliding surface of the rack slot for engaging the lower side of the rack when the rack is in the final position within the rack slot, wherein the snap fit device may not protrude from the sliding surface when the rack is loaded into the rack slot and not in the final position. Thus, engaging the lower side by the snap fit device is provided by protruding from the sliding surface and disengaging is provided by not protruding from the sliding surface. Particularly, unless the rack is in the final position, the lower side of the rack presses the snap fit device downwards in the retracted position such that the snap fit device does not obstruct the inserting or loading of the rack into the rack slot.

The method of the present disclosure may also comprise reading a rack identification, a position identification, an identification of a sample, reagent or consumable provided in the rack and/or a compartment identification of the rack by means of a bar code reader. Thus, the analyzer is configured to obtain different information directly or indirectly associated with the rack by means of the bar code reader as bar codes are commonly used with racks, samples stored therein and the like.

The method may further comprise detecting whether the rack is in the final position by means of a sensor. Thus, the analyzing process will only be initiated if the rack is completely and correctly inserted into the rack slot.

The sensor may trigger a reading process of the bar code reader. Thus, the bar code reader is only activated if the sensor indicates that the rack is completely and correctly inserted into the rack slot. Thereby, any potential reading errors are prevented. Further, energy may be saved if the bar code reader is not permanently activated.

The sensor may detect whether the rack is in the final position by means of detecting a compressed state of the spring device. Thus, the spring device indicates the final position of the rack if the spring device is compressed.

The spring device may comprise a plunger and a plunger rod moveable together with the spring device, wherein the sensor may detect the compressed state of the spring device by means of detecting the plunger rod. Thus, depending on whether the plunger rod is detected or not, the sensor is capable to indicate whether the rack is in the final position or not.

The sensor may be a light barrier and may comprise a light emitter and a light receiver, wherein the light emitter may emit light on a light path towards the light receiver, wherein the light barrier may detect the plunger rod if the light receiver does not receive light from the light emitter. Thus, if the light receiver does not receive light, the sensor indicates that the rack is in the final position. Accordingly, in a simple manner, the correct and complete insertion of the rack into the rack slot may be detected.

The plunger rod may be moved such that the light path is interrupted when the rack is in the final position. Thus, an interruption of the light path indicates the final position of the rack and if the plunger rod exposes the light path, this indicates that the rack is not fully received in the rack slot.

The light barrier may trigger the reading process of the bar code reader if the light barrier detects that the rack is in the final position. Thus, the bar code reader is only activated if the sensor indicates that the rack is completely and correctly inserted into the rack slot. Thereby, any potential reading errors are prevented. Further, energy may be saved if the bar code reader is not permanently activated. Accordingly, a user friendly loading concept of a rack into the rack slot of the analyzer is provided.

According to the present disclosure, a system comprises an analyzer as described above operably connected to a computer controller configured to control a loading process of a rack into the rack slot of the analyzer. Thus, a software based approach for controlling the loading and unloading of the rack is provided.

The computer controller may be configured to detect whether the rack is in the final position. Thus, the user friendliness is enhanced.

The analyzer may comprise a sensor configured to detect whether the rack is in the final position, wherein the sensor is operably connected to the computer controller. Thus, a computer based supervision of the loading process is provided and a user does not have to check the correct loading.

The analyzer may comprise a bar code reader for reading a rack identification, a position identification, an identification of a sample, a reagent or a consumable provided in the rack and/or a compartment identification of the rack by means of a bar code reader, wherein the bar code reader may be connected to the computer controller. Thus, the analyzer may obtain a lot of information by means of the bar code reader and the computer controller. Particularly, the computer controller may handle the information provided by the bar code reader.

The sensor may be configured to trigger the bar code reader if the rack is in the final position. Thus, the bar code reader is only activated if the sensor indicates that the rack is completely and correctly inserted into the rack slot. Thereby, any potential reading errors are prevented. Further, energy may be saved if the bar code reader is not permanently activated.

The system may further comprise a signalizing device configured to signalize a correct and/or incorrect loading of the rack. Thus, the system may provide a feedback of the loading process to an user.

Thus, an exemplary embodiment provides that the whole loading and unloading is controlled by software. It checks whether the rack has been loaded correctly by comparing the scanned results versus the expected results. It buffers the read barcodes and compares the completeness of the content in case the end position has been reached. The signal of the light barrier needs to be stable for a defined interval to start the completeness check mentioned above. This enhances the user friendliness, as the loading gets more robust. The check for completeness is only been done at the end, thus the movement of the rack does not matter, i.e. if the rack get loaded in front direction, moved backwards during the loading and moved forward again until the end position has been reached. The software may further check whether the correct slot, i.e. the expected or target slot, has been loaded by analyzing the light barrier feedback, as the light barrier is directly linked with the corresponding rack slot identification.

In case the light barrier gets deactivated after the loading process has been successfully completed, which means the rack got lifted and released from its snap fit position, the whole loading process gets invalid, and the user may be asked to load the rack again over the output means. In case the completeness check of the data buffer is not successful, e.g. missing data due to not correctly arranged sample barcodes or not read barcodes because of too fast rack movement of user, the reading process gets rejected, and the user may get informed via a touchscreen or other output means. Once the rack slots are loaded and the user triggers a safety lock of a cover of the analyzer via input means so as to close the analyzer, the reading of the barcode scanner gets terminated.

The concept described can have one barcode scanner per single rack slot. However it is also possible to use the concept with one barcode scanner reading multiple rack slots. Based on the technical properties of the barcode scanner and depending on the arrangement of the components, an additional sensor per rack slot positioned at the very front of each rack slot may be required to adjust the focus of the barcode scanner to the corresponding rack slot reading distance. Hence, the rack slot identification has to be identified before the rack gets read.

FIG. 1 shows an enlarged view of an analyzer 100. The analyzer 100 comprises at least one rack slot 102. The rack slot 102 is configured to receive at least one rack 104. Basically, the rack 104 may be designed as described in EP 0 738 541 B1, the contents of which concerning the formation of the rack is incorporated herein by reference. The rack slot 104 comprises a front end 106, at which the rack 104 is manually loadable into the rack slot 102, and a rear end 108, which is opposite to the front end 106 and at which the rack 104 is fully receivable in the rack slot 102. The rack slot 102 is configured such that the rack 104 is movable between the front end 106 and the rear end 108 in a longitudinal direction. With other words, the rack slot 102 extends in a longitudinal direction from the front end 106 to the rear end 108. Thus, the rack slot 102 comprises a longitudinal shape with a length significantly greater than a width thereof. For this purpose, the rack slot 102 comprises a sliding surface 110 on which the rack 104 is slidably movable between the front 106 and the rear end 108.

FIG. 2 shows a side view of the rack slot 102. FIG. 3 shows a further side view of the rack slot 102. Particularly, FIG. 2 shows the rack 104 disposed at the front end 106 such that the rack 104 is not fully received in the rack slot 102. FIG. 3 shows the rack 104 at the rear end 108 such that the rack 104 is fully received in the rack slot 102. In other words, FIG. 3 shows the rack 104 being completely arranged in the rack slot 102 while one of its ends is located at the rear end 108.

The analyzer 100 further comprises a spring device 112. The spring device 112 is arranged at the rear end 108. The spring device 112 is configured to provide a biasing force towards the front end 106. The biasing force is adapted to move the rack 104 towards the front end 106 if the rack 104 is not fully received in the rack slot 102. Thus, the biasing force is adjusted by selecting an appropriate material and spring constant of the spring device 112 so as to overcome the weight force of the rack 104 and the frictional force of the rack 104 along the sliding surface 110. The spring device 112 is further configured to fix the rack 104 in a final position if the rack 104 is fully received in the rack slot 102 as will be described in further detail below.

Figure 4:
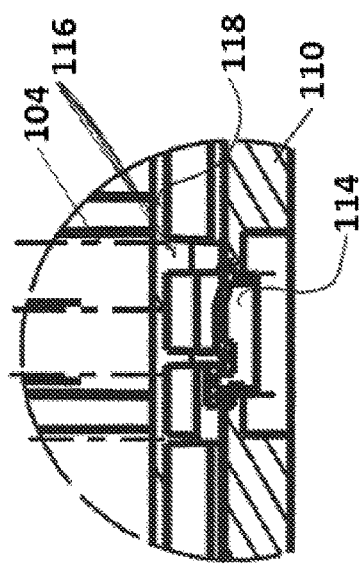
FIG. 4 shows an enlarged view of detail A of FIG. 3.

FIG. 4 shows an enlarged view of detail A of FIG. 3. The rack slot 102 comprises an elastic snap fit device 114. The snap fit device 114 is configured to engage the rack 104 if the rack 104 is in the final position. As shown in FIG. 4, the snap fit device 114 is configured to engage a depression 116 on a lower side 118 of the rack 104. For this purpose, the snap fit device 114 is moveable between a protruded position, in which the snap fit device 114 protrudes from the sliding surface 110 for engaging the lower side 118 of the rack 104 if the rack 104 is in the final position, and a retracted position in which the snap fit device 114 does not protrude from the sliding surface 110 if the rack 104 is loaded into the rack slot 102 and not in the final position. The snap fit device 114 is arranged adjacent to the front end 106. The spring device 112 is configured to fix the rack 104 in the final position by means of pushing the rack 104 against the snap fit device 114.

Figure 5:
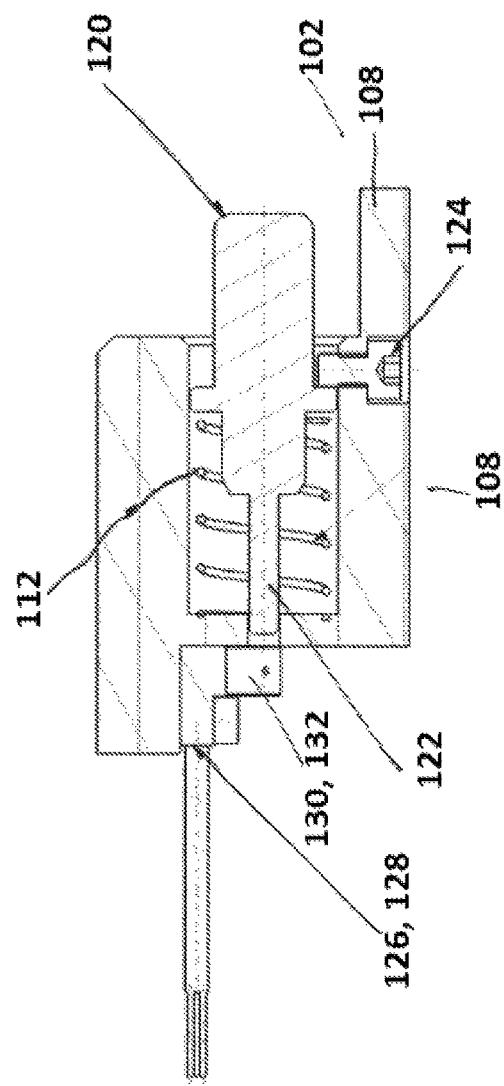
FIG. 5 shows an enlarged view of detail B of FIG. 3.

FIG. 5 shows an enlarged view of detail B of FIG. 3. FIG. 6 shows a further enlarged view of detail B of FIG. 3. Particularly, FIG. 5 shows the spring device 112 in an expanded position when the rack 104 is not fully received in the rack slot 102 and FIG. 6 shows the spring device 112 when the rack 104 is in the final position within the rack slot 102. As shown in FIGS. 5 and 6, the spring device 112 comprises a plunger 120 and a plunger rod 122. The plunger 120 and the plunger rod 122 may be integrally formed. The plunger 120 and the plunger rod 122 are moveable together with the spring device 112. For this purpose, the plunger 120 and the plunger rod 122 may be connected or fixed to the spring device 112. Below the plunger 120, the rack slot 102 comprises a stopper element 124 such as a screw configured to prevent an excessive movement of the plunger 120 towards the front end 106.

The analyzer 100 further comprises a sensor 126 configured to detect whether the rack 104 is in the final position. The sensor 126 is arranged adjacent to the rear end 108. Particularly, the sensor 126 is configured to detect whether the rack 104 is in the final position by means of detecting a compressed state of the spring device 112. For example, the sensor 126 is a light barrier 128. The light barrier 128 is configured to detect the compressed state of the spring device 112 by means of detecting the plunger rod 122. For this purpose, the light barrier 128 comprises a light emitter 130 and a light receiver 132. The light emitter 130 is configured to emit light on a light path towards the light receiver 132. With respect to the illustration of FIGS. 5 and 6, the light path is perpendicular to the drawing plane. The light barrier 128 is configured to detect the plunger rod 122 if the light receiver 132 is not capable of receiving light from the light emitter 130. Thus, the plunger rod 122 is moveable such that the light path is interruptible. Particularly, the plunger rod 122 is configured to be moved through a gap between the light emitter 130 and the light emitter 132. With other words, if the light receiver 132 receives light emitted from the light emitter 130, the light barrier 128 does not detect the plunger rod 122 as the light path is not interrupted thereby. To the contrary, if the light receiver 132 does not receive light emitted from the light emitter 130, the light barrier 128 detects the plunger rod 122 and the light path is interrupted thereby. Alternatively, the plunger rod 122 may comprise an orifice such as a slot through which light may pass. The orifice may be positioned at the plunger rod 122 such that the light emitted from the light emitter 130 may pass through the orifice and propagate to the light receiver 132 when the spring device 112 is in the compressed state and may not pass through the orifice when the spring device 112 is in the expanded state.

The analyzer 100 further comprises a bar code reader 134 configured to read a bar code on a rack, sample or reagent vessel or consumable. The bar code on each component includes identification information that identifies that component and/or its contents. The bar code on each component and/or subcomponent is referred to herein as rack identification, position identification, sample, reagent, or consumable identification, and/or compartment identification. The bar code reader 134 serves for reading a rack identification, a position identification, an identification of a sample, reagent or consumable provided in the rack 104, and/or a compartment identification of the rack 104. The light barrier 128 is configured to trigger the reading process of the bar code reader 134 and the light barrier 128 detects that the rack 104 is in the final position. With other words, the bar code reader 134 is exclusively activated if the rack 104 is correctly or fully received in the rack slot 102.

Hereinafter, a method for loading a rack 104 into the rack slot 102 of the analyzer 100 will be described. At the beginning of the method, a user initiates the loading process on an input means of the analyzer 100 such as a touchscreen. Thereby, a safety lock of a cover for the at least one rack slot 102 opens (not shown in detail). Then, the rack 104 is manually loaded at the front end 106 of the rack slot 102 such as by the user of the analyzer 100. With other words, the rack 104 is disposed on the sliding surface 110 at the front end 106 with an end of the rack 104 facing the rear end 108 of the rack slot 102. Thus, the rack 102 is disposed on the sliding surface 110 only with a portion of its lower side 118. This step is shown in FIG. 2.

In this state, the snap fit device 114 does not protrude from the sliding surface 110 but is pressed downwards by the lower side 118 of the rack 104. Thus, the snap fit device 114 does not engage the depression 116. Further, as shown in FIG. 5, the spring device 112 is in the expanded state and the plunger rod 122 does not interrupt the light path from the light emitter 130 to the light receiver 132. Thus, the light receiver 132 receives light emitted from the light emitter 130. Accordingly, the bar code reader 134 is not triggered. Then, the rack 104 is manually moved to the rear end 108 of the rack slot 102 against the biasing force of the spring device 112. With other words, the user of the analyzer 100 has to move the rack 104 with a force higher than the biasing force of the spring device 112 in order to allow the rack 104 to be moved to the rear end 108. Thereby, the spring device 112 is compressed.

If the rack 104 is fully received in the rack slot 102, the rack 104 is fixed in the final position by means of the spring device 112. Particularly, the spring device 112 pushes the rack 104 against the elastic snap fit device 114 which now protrudes from the sliding surface 110 and engages the depression 116. This state is shown in FIG. 3. It is to be noted that if the rack 104 is not fully received in the rack slot 102, the spring device 112 pushes the rack 104 towards the front end 106 by means of the biasing force such that the user of the analyzer 100 receives a physical feedback that the rack 104 is not correctly inserted into the rack slot 102.

If the rack 104 is in the final position, the plunger rod 122 is moved integrally with the spring device 112 and interrupts the light path from the light emitter 130 to the light receiver 132. Thus, the light receiver 132 does not receive light emitted from the light emitter 130 and the light barrier 128 detects the compressed state of the spring device 112. Accordingly, the sensor 126 outputs a signal indicating that the rack 104 is correctly inserted in the rack slot 102. Thereby, the bar code reader 134 is triggered and the reading process thereof is initiated. Thus, the bar code reader 134 reads a rack identification, a position identification, an identification of a sample, reagent or consumable provided in the rack 104, and/or a compartment identification of the rack 104. To unload the rack 104, the user needs to lift the whole rack 104 to release it from the snap fit device 114. The spring device 112 expands and pushes the rack to the front end 106 such that the user may remove the rack from the rack slot 102. Once the snap fit has been overcome, the light barrier 128 may become deactivated.

Hereinafter, a further optional embodiment will be described. The further embodiment relates to a system 136 comprising the analyzer 100 and a computer controller 138 configured to control the loading process of the rack 104 into the rack slot 102 of the analyzer 100. Particularly, the computer controller 138 is configured to detect whether the rack 104 is in the final position. The sensor 126 may be connected to the computer controller 138. Further, the bar code reader 134 may be connected to the computer controller 138. The system 136 may further comprise a signalizing device 140 configured to signalize a correct and/or incorrect loading of the rack 104. The signalizing device 140 may be an acoustic device giving an acoustic feedback to the user. Alternatively, the signalizing device 140 may be a visual device such as the touchscreen giving a visual feedback to the operator of the analyzer 100. The method steps for loading the rack 104 into the rack slot 102 are identical to those describes before.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims.

Various publications are cited herein, the disclosures of which are incorporated by reference in their entireties.

LIST OF REFERENCE NUMBERS 100 analyzer
102 rack slot
104 rack
106 front end
108 rear end
110 sliding surface
112 spring device
114 snap fit device
116 depression
118 lower side
120 plunger
122 plunger rod
124 stopper element
126 sensor
128 light barrier
130 light emitter
132 light receiver
134 bar code reader
136 system
138 computer controller
140 signalizing device

The invention claimed is:

1. An analyzer comprising a rack slot configured to receive a rack, wherein the rack slot comprises:
   a front end adapted to manually receive the rack,
   a rear end opposite the front end, and
   a spring device positioned at the rear end, wherein the spring device provides a biasing force towards the front end to move the rack towards the front end and thereby position and fix the rack in the rack slot if the rack is fully received in the rack slot, and wherein the rack slot further comprises an elastic snap fit device adjacent the front end to engage the rack in a snap fit arrangement when the rack is positioned in the rack slot.

2. The analyzer according to claim 1, wherein the rack slot is configured such that the rack is moveable between the front end and the rear end in a longitudinal direction.

3. The analyzer according to claim 1, wherein the spring device positions the rack in the rack slot by pushing the rack against the snap fit device.

4. The analyzer according to claim 1, wherein the snap fit device is adjacent the front end.

5. The analyzer according to claim 1, further comprising a bar code reader for reading a rack identification, a position identification, an identification of a sample, reagent or consumable provided in the rack and/or a compartment identification of the rack.

6. The analyzer according to claim 5, further comprising a sensor configured to detect whether the rack is positioned in the rack slot.

7. The analyzer according to claim 6, wherein the sensor is operably connected to the bar code reader and the bar code reader reads one or more of said rack identification, position identification, compartment identification, and sample, reagent or consumable identification when the sensor detects the rack in position in the rack slot.

8. The analyzer according to claim 6, wherein the sensor is arranged adjacent the rear end.

9. The analyzer according to claim 8, wherein the sensor detects a compressed state of the spring device.

10. The analyzer according to claim 6, wherein the sensor is a light barrier.

11. The analyzer according to claim 10, wherein the spring device comprises a plunger and a plunger rod moveable together with the spring device, wherein the light barrier detects the compressed state of the spring device by detecting the plunger rod.

12. A method for loading a rack into a rack slot of an analyzer according to claim 1, comprising:
   (a) loading, manually, a rack at the front end of the rack slot,
   (b) moving, manually, the rack to the rear end of the rack slot against the biasing force of the spring device, and
   (c) fixing the rack in position by means of the spring device when the rack is fully received in the rack slot.

13. A system comprising an analyzer according to claim 1 and a computer controller configured to control a loading process of a rack into the rack slot of the analyzer.

14. The system according to claim 13, further comprising a signalizing device configured to signal a correct and/or incorrect loading of the rack.

* * * * *